United States Patent [19]
Sifniades et al.

[11] Patent Number: 5,948,908
[45] Date of Patent: *Sep. 7, 1999

[54] PROCESS FOR DEPOLYMERIZING POLYCAPROLACTAM PROCESSING WASTE TO FORM CAPROLACTAM

[75] Inventors: Stylianos Sifniades, Madison; Alan Bart Levy, Randolph, both of N.J.

[73] Assignee: AlliedSignal Inc., Morristown, N.J.

[*] Notice: This patent issued on a continued prosecution application filed under 37 CFR 1.53(d), and is subject to the twenty year patent term provisions of 35 U.S.C. 154(a)(2).

[21] Appl. No.: 08/617,448

[22] Filed: Mar. 18, 1996

[51] Int. Cl.⁶ .................................................. C07D 201/12
[52] U.S. Cl. .................................................. 540/540
[58] Field of Search ............................................. 540/540

[56] References Cited

U.S. PATENT DOCUMENTS

| | | | |
|---|---|---|---|
| 2,343,174 | 2/1944 | Edison et al. | 526/65 |
| 2,348,751 | 5/1944 | Peterson | 528/499 |
| 3,182,055 | 5/1965 | Bonfield et al. | 260/239.3 |
| 3,317,519 | 5/1967 | Lazarus et al. | 540/533 |
| 3,939,153 | 2/1976 | Fowler | 260/239 |
| 3,988,406 | 10/1976 | Nakamura et al. | 264/68 |
| 4,051,212 | 9/1977 | Grigat et al. | 264/122 |
| 4,107,160 | 8/1978 | Dicoi et al. | 260/239 |
| 4,605,762 | 8/1986 | Mandoki | 51/487 |
| 5,169,870 | 12/1992 | Corbin et al. | 521/49.8 |
| 5,233,037 | 8/1993 | Nielinger et al. | 540/540 |
| 5,294,707 | 3/1994 | Kotek | 540/540 |
| 5,359,062 | 10/1994 | Fuchs et al. | 540/540 |
| 5,360,905 | 11/1994 | Fuchs et al. | 540/540 |
| 5,455,346 | 10/1995 | Kopietz et al. | 540/540 |
| 5,457,197 | 10/1995 | Sifniades et al. | 540/540 |
| 5,468,900 | 11/1995 | Moran et al. | 562/590 |
| 5,495,014 | 2/1996 | Fuchs et al. | 540/538 |
| 5,495,015 | 2/1996 | Bassler et al. | 540/540 |

FOREIGN PATENT DOCUMENTS

| | | |
|---|---|---|
| 608454 | 3/1994 | European Pat. Off. .......... 540/540 |
| 627417A1 | 12/1994 | European Pat. Off. . |
| 0 676 394 | 3/1995 | European Pat. Off. . |
| 4421239A1 | 6/1994 | Germany .......... 540/540 |
| 13636 | 5/1978 | Japan . |
| 60-20379 | 5/1985 | Japan . |
| 793598 | 4/1958 | United Kingdom . |
| 1017985 | 1/1966 | United Kingdom . |

OTHER PUBLICATIONS

Translation of H. Ludewig et al., "Work–Up of Polyamide (Perlon, Nylon, Trelon) Wastes According to the Depolymerization–Filtration Method", *Faserforschung und Texiletechnik 5(7)*, pp. 277–284 (1954).

Chemical Abstracts 49, 9281h (1955).

N.D. Katorzhnov et al., "Effect of Average Molecular Weight of the Polymer on the Rate of Caprolactam Formation during Thermal Depolymerization of Unstabilized Polycaprolactam", *Prikl. Chim. 32*, pp. 655–658 (Aug. 16, 1957).

N.D. Katorzhnov et al., "Reaction Mechanism of the Thermal Depolymerization of Polycaprolactam", *Prikl. Chim. 32*, pp. 1395–1399 (May 8, 1958).

S.Smith, "The Re–Equilibration of Polycaproamide", *Journal of Polymer Science XXX*, pp. 459–478 (1958).

Translation of F. Mikula et al., "Depolymerization of Polycaprolactam Wastes to Monomeric 6–Caprolactam", *Chemicky Prumysl. 17/42(3)*, pp. 132–137 (1967).

A.K. Mukherjee et al., "Depolymerization of Poly–ϵ–Caprolactam Catalyzed by Sodium Hydroxide", *Journal of Applied Polymer Science 22*, pp. 361–368 (1978).

Chemical Abstracts 94, 16433y (1980).

T. Ohtsubo, "Studies on the Depolymerization of Polycaproamide—Part 1—Depolymerization of Polycaproamide Using Phosphoric Acid as the Catalyst Under Steam Blowing", *Nippon Kagakkaishi 2*, 337 (1974) and translation thereof.

K. Petru et al., "Depolymerization of Polycaprolactam Wastes", *Chemicky Prumysl 24/49 (7–8)*, 394–396 (1974) and translation thereof.

Chem. Ing. Techn, 45, 1509–1524 (1973); (Translation copy).

L.A. Dmitrieva et al., Fiber Chemistry, vol. 17, No. 4, Mar. 1986, pp. 229–241 (English journal translation of Khimicheski Volokna, No. 4 pp. 5–12, Jul.–Aug., 1985).

*Primary Examiner*—Richard L. Raymond
*Attorney, Agent, or Firm*—Melanie L. Brown; Virginia S. Andrews; Roger H. Criss

[57] ABSTRACT

The present invention provides an improved process for the recovery of caprolactam from polycaprolactam processing waste. The present process for depolymerizing polycaprolactam waste to form caprolactam comprises the step of: in the absence of added catalyst, contacting the polycaprolactam waste with superheated steam at a temperature of about 250° C. to about 400° C. and at a pressure within the range of about 1.5 atm to about 100 atm and substantially less than the saturated vapor pressure of water at the temperature wherein a caprolactam-containing vapor stream is formed.

20 Claims, 2 Drawing Sheets

PROCESS FOR DEPOLYMERIZING POLYCAPROLACTAM PROCESSING WASTE TO FORM CAPROLACTAM

BACKGROUND OF THE INVENTION

The present invention relates to a process for the depolymerization of polycaprolactam processing waste to form caprolactam.

The processing of polycaprolactam into intermediate articles such as fiber, chip, film, or molded articles results in polycaprolactam (hereinafter "nylon 6") processing waste, i.e., scrap nylon 6 polymeric and/or oligomeric materials. Examples of such scrap nylon 6 polymeric and/or oligomeric material are yarn waste, chip waste, or extruder slag. Examples of scrap nylon 6 oligomeric materials are the linear and cyclic oligomers of caprolactam. The nylon 6 intermediate articles are then incorporated or transformed into end use products such as fabrics, engineered plasics, carpets, and packaging.

The current worldwide production of polycaprolactam is enormous and this polycaprolactam is then processed into the intermediate articles. The scrap nylon 6 which results from this polycaprolactam processing into intermediate articles is sizeable.

In order to improve the yield in the processing of polycaprolactam, the scrap nylon 6 materials are depolymerized to caprolactam and the caprolactam is then reused. Recovery of caprolactam from polycaprolactam processing waste scrap, i.e. nylon 6 which is substantially free of non-nylon 6 materials, has been practiced for at least twenty years. In general, nylon 6 is depolymerized by heating at elevated temperatures, usually in the presence of a catalyst and/or steam. See U.S. Pat. Nos. 4,107,160; 5,233,037; 5,294,707; 5,359,062; 5,360,905; 5,468,900; German 4,421,239A1; Example 5 of European Patent Application 608,454; and *Chem. Ing. Techn.* 45, 1509 (1973). The caprolactam produced may be removed as a vapor stream as taught by AlliedSignal's U.S. Pat. No. 3,182,055. In most of the above processes a catalyst such as phosphoric acid is used to promote depolymerization of polycaprolactam. An extensive review of the field has been given by L. A. Dmitrieva et al, Fibre Chemistry, Vol. 17, No. 4, March 1986, pp. 229–241. U.S. Pat. No. 5,495,014 teaches the depolymerization of nylon 6 wherein the reaction is in the liquid phase at elevated temperatures in the presence of a heterogeneous catalyst and in organic solvent.

U.S. Pat. No. 3,939,153 to Fowler teaches a polycaprolactam depolymerization process wherein superheated steam and melted scrap nylon 6 are combined in a tubular elongated reactor. The reference teaches that the average temperature in the reactor is about 343° C. to about 677° C., the average residence time for the nylon melt in the reactor is from about one to about 40 minutes, and the average residence time for the superheated steam in the reactor is from about 0.01 to about ten seconds. The reference makes no mention of pressure in the reactor. The steam and nylon melt decomposition product then pass as a combined stream out of the reactor into a nylon column wherein the steam and nylon decomposition products pass overhead in vapor phase and the unconverted nylon 6 and byproduct oligomers are withdrawn from the nylon column and recycled back to the feed tank. The reference teaches that in a typical system, about 20% of the nylon 6 passing through the reactor is depolymerized to caprolactam and the remainder is recycled back to the feed tank.

The Fowler polycaprolactam depolymerization process which has only a 20% first pass yield is unacceptable in industry. Additionally, we have found that under the process conditions employed by Fowler, relatively large amounts of caprolactam cyclic dimer and ammonia are produced. Thus, a need exists in the industry for an improved process for the depolymerization of polycaprolactam processing waste.

SUMMARY OF THE INVENTION

The invention provides an improved process for depolymerizing polycaprolactam waste to form caprolactam. The process comprises the step of: in the absence of added catalyst, contacting polycaprolactam waste with superheated steam at a temperature of about 250° C. to about 400° C. and at a pressure within the range of about 1.5 atm to about 100 atm and substantially less than the saturated vapor pressure of water at the temperature wherein a caprolactam-containing vapor stream is formed.

Optionally, the polycaprolactam waste is contacted for a short time period with liquid water under elevated temperatures and pressures for time sufficient to reduce the molecular weight of the polycaprolactam, prior to contacting with steam as discussed above.

BRIEF DESCRIPTION OF THE DRAWING

The invention will be described in more detail below with reference to drawings, wherein

FIG. 1 illustrates at a temperature of 320° C. the effect of pressure on caprolactam production.

FIG. 2 illustrates at a temperature of 320° C. the effect of pressure on caprolactam, ammonia, and cyclic dimer production.

FIG. 3 illustrates at a temperature of 340° C. the effect of pressure on caprolactam, ammonia, and cyclic dimer production.

DETAILED DESCRIPTION OF THE PREFERRED EMBODIMENTS

Figure 1:
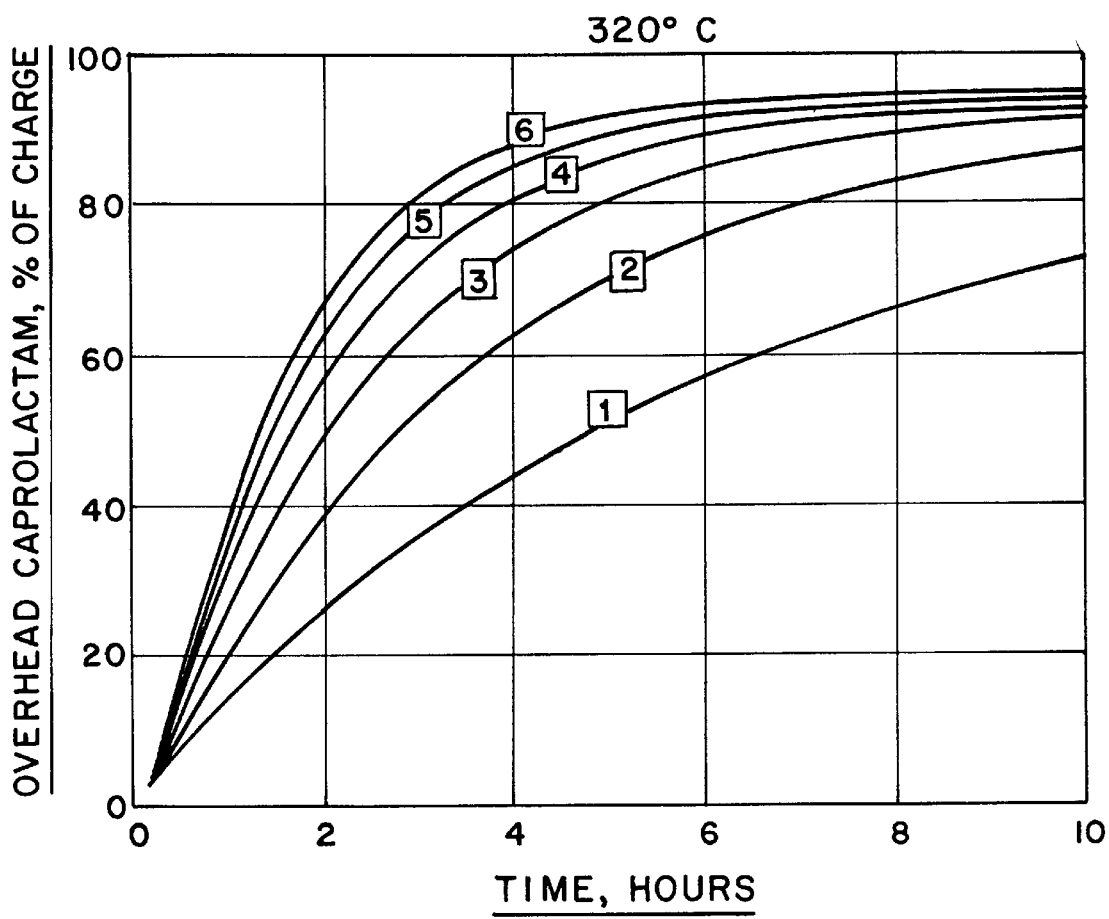
FIG. 1 through 3 are graphs illustrating advantages of the present invention.

The term "polycaprolactam waste" as used herein means scrap nylon 6 polymeric and/or oligomeric material. Examples of scrap nylon 6 oligomeric materials are linear and cyclic oligomers of caprolactam. Such scrap nylon 6 polymeric and/or oligomeric material is generated during the production of intermediate articles such as fiber, chip, film, or molded articles. The nylon 6 intermediate articles are then incorporated or transformed into end use multi-component products such as fabrics, engineered plastics, carpets, and packaging. Examples of such scrap nylon 6 polymeric and/or oligomeric material are yarn waste, chip waste, or extruder slag. The term "polycaprolactam waste" excludes the presence of non-polycaprolactam components in significant amounts. However, it does not exclude small amounts of adventitious contaminants, such as environmental dust or humidity, or processing oils and lubricants, or fiber opacifiers such as titanium dioxide. Such non-polycaprolactam components will generally be present in no more than about 10% by weight with respect to polycaprolactam.

The term "fiber" as used herein means an elongated body wherein the length dimension is much greater than the transverse dimensions of width and thickness. Accordingly, "fiber" includes, for example, monofilament, multifilament yarn (continuous or staple), ribbon, strip, staple and other forms of chopped, cut or discontinuous fiber, and the like having regular or irregular cross-sections. "Fiber" includes a plurality of any one of the above or a combination of the above.

According to the process of the current invention, caprolactam is formed by contacting the polycaprolactam waste with superheated steam at elevated temperatures and superatmospheric pressures and removing a vapor stream containing caprolactam from the contact region. The term "superheated steam" as used herein means steam that is heated to a temperature substantially higher than the temperature at which condensation to liquid water would take place at the pressure used to convey said steam. An important benefit of the process is that no catalyst is needed for recovering caprolactam from polycaprolactam waste.

Accordingly, for the present process, no acidic catalyst is added to the vessel in which the polycaprolactam waste is contacted with superheated steam. It should be understood, however, that the waste material feedstock may include minor amounts of materials (for example, contaminants) that incidentally are recognized in the art as catalysts. However, the subject process does not rely on the presence or addition of any such catalytic materials in the vessel.

The polycaprolactam waste is preferably fed to the reactor as a melt. This feeding may be achieved by using an extruder, gear pump, or other means known in the art. Some feeding systems, such as extruders, allow the development of relatively high pressures in the melt. This offers the option of contacting the melt with liquid water at elevated temperatures for a short period of time at little added cost. This may be achieved, for example, by introducing water under pressure in the extruder barrel. The contact time between the melt and water may be extended by placing a high pressure pipe between the extruder exit and reactor. In this optional pretreatment step, the polycaprolactam waste is combined with liquid water and heated at a sufficient temperature for a time period sufficient to effect an initial depolymerization of the polycaprolactam waste. The depolymerization products formed in this step may include reduced molecular weight polycaprolactam, caprolactam, caprolactam linear oligomers, and caprolactam cyclic oligomers. Such contact accelerates caprolactam production in subsequent process steps as disclosed in AlliedSignal's U.S. Pat. No. 5,457,197 to Sifniades et al. The disclosure of AlliedSignal's U.S. Pat. No. 5,457,197 is incorporated herein by reference.

For the recovery of caprolactam to be economical, it is desirable to utilize as inexpensive equipment and as little steam as technically feasible. A good index of the economy of the process is the concentration of caprolactam obtained in the overheads, which bears an inverse relationship to the amount of steam used. Concentrations in excess of 15 weight percent may be obtained by appropriate design of the reactor and choice of operating conditions as described below.

The reaction temperature should be at least about 250° C. but not higher than about 400° C. Generally, the rate of caprolactam formation increases with increasing temperature. However, the rate of side reactions of nylon 6 such as evolution of ammonia also increases with temperature.

Temperatures of at least about 250° C. are preferred because below 250° C., caprolactam formation may be too slow. Temperatures no greater than about 400° C. are preferred, as above 400° C. side reactions of nylon 6 may become prohibitively fast. A preferred temperature range is about 280° C. to about 350° C., more preferably a temperature in the range of about 300° C. to about 340° C.

The pressure should be moderately above atmospheric but higher pressures offer certain advantages as will be explained below. Other factors, such as the availability and operating cost of high pressure equipment may influence the choice of pressure.

Regarding the effect of pressure, it has been found that for a given temperature and steam flow, increasing the reactor pressure generally increases the caprolactam concentration in the overheads up to an optimal pressure. Further small increases in pressure have little effect on caprolactam concentration. However, a large increase in pressure beyond the optimal pressure results in decreased caprolactam concentration. Generally, the higher the operating temperature, the higher is the optimal pressure at which maximum caprolactam concentration is obtained. For example, at an hourly steam flow equal to twice the mass of the polycaprolactam charged, the optimal pressure is about 17 atm (about 1720 kPa) at about 320° C. and about 19 atm (about 1920 kPa) at 340° C. Optimal pressure conditions under different operating conditions within the scope of this invention can be determined by those skilled in the art.

It will be appreciated that the optimal pressure is well below the saturated vapor pressure of water at the operating temperature. For example, the saturated vapor pressure of water is 111 atm at 320° C., and 144 atm at 340° C. Therefore, it is clear that in the current process, no liquid aqueous phase is present.

The effect of pressure on caprolactam concentration at constant steam flow is matched by its effect on the rate of production of caprolactam. Therefore, operating near the optimal pressure minimizes not only steam usage but also reactor volume.

A further benefit of operating close to the optimal pressure is the suppression of side reactions leading to ammonia formation. We have found that at a given temperature, ammonia production relative to caprolactam production is lowest at pressures close to the optimal pressure for caprolactam production as will be discussed later relative to FIG. 2.

Although not wishing to be bound by any theory, we wish to rationalize our findings by means of the following theory. One useful outcome of the theory is that it allows the construction of a computer model that may be used to optimize the process once sufficient data have been collected to calibrate the model. We believe that as pressure increases at a given temperature and steam flow, the amount of water that dissolves in nylon 6 is increased resulting in the acceleration of depolymerization reactions. It will be appreciated that the action of water in the depolymerization of nylon 6 to caprolactam is catalytic, that is, no net amount of water is consumed in the overall conversion of nylon 6 to caprolactam. Caprolactam is generally formed by cleavage of caprolactam molecules from the ends of the nylon 6 chain, in a reversal of the polyaddition reaction which constitutes caprolactam polymerization. Water promotes caprolactam formation by virtue of promoting the cleavage of amide bonds, which results in the formation of more end groups. Water is consumed only to the extent that some of the nylon 6 charged is not converted to caprolactam. As caprolactam is produced at a faster rate, its partial pressure in the vapor phase increases. However, the partial pressure of water also increases, approximately in proportion to the applied pressure. The caprolactam/water ratio in the overheads is proportional to the ratio of the corresponding vapor pressures.

Therefore, increasing the reactor pressure can result in an increase or a decrease of caprolactam concentration in the overheads, depending on whether the caprolactam vapor pressure increases faster or slower than the water vapor pressure. Evidently, at pressures below the optimal pressure, the caprolactam partial pressure increases faster than the partial pressure of water as the reactor pressure is increased. At pressures above the optimal pressure, the partial pressure of water increases faster than the partial pressure of caprolactam as the reactor pressure is increased.

A secondary effect of pressure is the suppression of caprolactam cyclic dimer. The dimer is formed reversibly along with caprolactam during nylon 6 depolymerization. When the depolymerization is carried out at atmospheric pressure, relatively large amounts of the dimer are found in the overheads, as much as 3–4 wt % of the caprolactam. Increasing the pressure decreases the ratio of dimer to caprolactam in the overheads. Since dimer formation is reversible, dimer that does not distill over is converted eventually to caprolactam. Suppressing dimer concentration in the overheads is beneficial not only from the point of view of product yield, but also because the dimer, when present at high concentrations, may be deposited as a solid and clog the transfer lines and the condenser.

In view of these findings, the operating pressure should range from about 1.5 atm up to about 100 atm (about 152 kPa to about 10130 kPa). However, the pressure should be substantially less than the saturation vapor pressure of water under the operating temperature to ensure that liquid water does not condense in the reactor. For example, at 300° C., the saturated vapor pressure of water is 85 atm. Operation at that temperature should be carried out at pressures ranging from about 1.5 atm to about 75 atm. For the preferred temperature range of about 280° C. to about 350° C., the preferred pressure range is about 2 atm to about 30 atm (about 203 kPa to about 3940 kPa). For the more preferred temperature range of about 290° C. to about 340° C., the preferred pressure range is about 3 atm to about 15 atm (about 304 kPa to about 1520 kPa). The rate of steam flow should be sufficient to remove caprolactam from the reactor, but not so high as to cause undue dilution of caprolactam in the overheads. Since a high caprolactam concentration in the overheads is desired, the steam flow should be proportional to the rate of production of caprolactam, which is generally proportional to the mass of nylon 6 charged and also increases with temperature.

The contact of the polycaprolactam waste with superheated steam is effected in a vessel designed to withstand the requisite temperature and pressure, as well as the corrosiveness of the reactants. Since no corrosive catalysts, such as acids, are required in this process, no special alloys are required, and a stainless steel vessel is adequate.

Good contact between steam and the polycaprolactam waste is essential for an effective operation. Such contact may be achieved by various means known generally in the art. As an example, steam may be sparged through the material using a multiplicity of inlets, for example, using a steam distributor. Improved contact may be achieved by including mechanical agitation in the reactor, for example, using a combination of rotating paddles and static fins.

The process of the current invention may be carried out either continuously or in batch fashion. In the latter case, the polycaprolactam waste is charged to the reactor all at once and steam is sparged continuously until most of the caprolactam has been recovered. Generally, in the batch process, caprolactam concentration in the overheads diminishes as the charge is depleted of nylon 6. Said concentration may be maintained at relatively high levels throughout the process by gradually increasing the temperature and/or decreasing the steam flow as the run process.

In a continuous process, both the polycaprolactam waste and the steam are fed continuously to the reactor. Caprolactam is recovered overhead, while a nylon 6 depleted melt is discharged from the bottoms. This melt is a mixture of low molecular weight polycaprolactam with polycaprolactam degradation products and with non-polycaprolactam materials, and their degradation products, that may have been present in the feed stream. The volume of the bottoms stream will depend on the purity of the polycaprolactam waste and the extent of caprolactam yield. Generally, yields of caprolactam should exceed 90%. Therefore, for substantially pure polycaprolactam waste, the bottoms stream is generally less than 10% of the feed stream.

To maintain a high caprolactam concentration in the overheads, it is desirable to run the steam countercurrent to the melt flow. This can be achieved by using a series of continuous stirred reactors (CSTRs) in which melt flows from the first reactor to the last while steam flows in the opposite direction. However, it is also possible to operate with steam crossflow or crosscurrent flow. In this mode, the melt flows from the first reactor to the last, whereas fresh steam is supplied to each reactor. If desired, the steam flow to each reactor may diminish as the nylon content of the melt diminishes. Although crossflow may generally result in higher overall consumption of steam, it is simpler to implement and may require lower capital investment.

In a preferred embodiment of the process, the polycaprolactam waste melt is fed at the top of a continuous flow reactor. Superheated steam is fed through a distributor at the bottom of the reactor countercurrent to the flow of the melt. A vapor stream containing caprolactam is collected at the top of the reactor and nylon 6 depleted melt exits at the bottom. The polycaprolactam waste may be fed by means of an extruder, gear pump, or other device. The reactor may be divided into several stages by means of baffles. Means may be provided for mechanical agitation in each stage. Heat is provided to the reactor mainly by means of the superheated steam. Additional heat may also be provided through the polycaprolactam waste feed, especially if an extruder is used, and through the wall of the reactor.

Caprolactam may be separated from other components of the distillate. The vapors from the reactor overhead may be sent to a partial condenser to obtain a condensate containing caprolactam. Caprolactam suitable for the production of fiber, film, or engineered resin may be obtained from this condensate by further purification including distillation, crystallization and other conventional techniques known in the art. For example, the caprolactam purification process of AlliedSignal's U.S. Pat. Nos. 2,813,858; 3,406,176 or 4,767,503 to Crescentini et al. may be used.

The purified caprolactam may then be used to make polycaprolactam using a known process such as disclosed in AlliedSignal's U.S. Pat. Nos. 3,294,756; 3,558,567; or 3,579,483. The polycaprolactam may then be used in known engineered materials such as disclosed in AlliedSignal's U.S. Pat. Nos. 4,160,790; 4,902,749; or 5,162,440; spun into fiber using a known process such as disclosed in AlliedSignal's U.S. Pat. Nos. 3,489,832; 3,517,412; or 3,619,452; or made into film.

The following examples illustrate various preferred embodiments of the invention.

EXAMPLE 1

Nylon 6 chips, 15 g, having a molecular weight of about 20,000, were charged to a stainless steel cylindrical reactor of 24.5 mm diameter and 300 mm height. The reactor was connected to a condenser equipped with a back-pressure valve set at 6.4 atm (650 kPa). Superheated steam was blown through the bottom of the reactor at the rate of 0.4 g per minute while the temperature was maintained at 330° C. A small stream of nitrogen, 30 mL(STP)/min, was mixed with the steam to prevent backing of melt into the steam line. Overhead cuts were collected periodically and analyzed for caprolactam. After 225 min of operation, the combined overheads contained 12.0 g caprolactam.

EXAMPLE 2

Effect of Prehydrolysis on the Rate of Depolymerization

Nylon 6 chips, 15 g, having a molecular weight of about 20,000, and 7 g water were charged to a stainless steel cylindrical reactor of 24.5 mm diameter and 300 mm height. The reactor was sealed and the temperature was raised rapidly to 290° C. and held for 10 min. The molecular weight of the mixture (excluding caprolactam) was about 1,000 and the amount of caprolactam present was about 20% of the total amount of caprolactam theoretically recoverable from the amount of nylon 6 charged. The reactor was next cooled to 100° C. and connected to a condenser equipped with a back-pressure valve set at 6.4 atm (650 kPa). Superheated steam was blown through the bottom of the reactor at the rate of 0.4 g per minute while the temperature was maintained at 330° C. A small stream of nitrogen, 30 mL(STP)/min, was mixed with the steam to prevent backing of melt into the steam line. Overhead cuts were collected periodically and analyzed for caprolactam cyclic oligomers of caprolactam. After 225 min of operation, the combined overheads contained 14.6 g caprolactam, 0.098 g cyclic dimer, and 0.0058 g cyclic trimer.

COMPARATIVE EXAMPLE

Effect of Pressure on the Rate and Selectivity of Depolymerization

The procedure of Example 2 was repeated, except that the pressure was maintained at 1 atm (101 kPa). At the end of 225 min, the combined overheads contained 7.8 g caprolactam, 0.16 g cyclic dimer, and 0.060 g cyclic trimer.

EXAMPLE 3

Nylon 6 melt was charged via an extruder to a 2 L cylindical stainless steel reactor. The reactor was agitated by means of a down flow helical agitator that scraped the reactor walls and was equipped with two circular windows at mid-height that allowed observation of the reaction mass. The reactor vent was connected to a condenser via a back-pressure regulator. Superheated steam was blown throughout the operation at the rate of 35 to 40 g/min via a sparger at the bottom of the reactor and caprolactam containing vapor was drawn overhead and condensed. The pressure and temperature in the reactor were maintained at about 312° C. and 9.2 atm respectively. During the first 105 min of operation, 1100 g of nylon 6 were charged to the reactor at the rate of 10 to 12 g/min. At that point, the mass in the reactor was estimated at about 700 g. Feeding of nylon 6 was then interrupted for 120 min. The mass remaining in the reactor at that point was about 150 g. An additional 900 g nylon 6 was added during the next 45 min and the operation continued for an additional 60 min after termination of the second nylon 6 addition. The total amount of caprolactam found in the overheads condensate was 1558 g. The remaining melt that was drained from the reactor was 440 g and consisted essentially of low molecular weight nylon 6. The instantaneous rate of caprolactam production was roughly proportional to the amount of melt held in the reactor. The normalized rate of caprolactam production was about 0.7 to 0.8 g caprolactam per gram of melt held in the reactor per hour. The overall concentration of caprolactam was 11% by weight.

EXAMPLE 4

The apparatus of Example 3 was used. Nylon 6 melt was fed to the reactor throughout the run at a rate adjusted to maintain the melt level in the reactor at about 800 g, while superheated steam was blown at the rate of 4,000 g/h. The temperature and pressure were held at about 310° C. and 9.2 atm respectively. The run lasted for 6 hours. The rate of caprolactam production was 500 to 600 g/h, or 0.62 to 0.75 grams per gram of melt held in the reactor per hour. The overall concentration of caprolactam was 11% by weight.

EXAMPLE 5

A tube reactor of 24.5 mm diameter and 1070 mm height was charged with 100 g nylon 6 and steam was blown through the bottom. Overheads were collected at time intervals during the operation and analyzed for caprolactam, caprolactam cyclic dimer, and ammonia. Runs were carried out at various temperatures, pressures, and steam flows. The data were used to construct a computer model of the process in the framework of the theory presented earlier. The model was then used to draw the curves shown in FIGS. 1 through 3. In all Figures, an hourly steam flow equal to twice the mass of the polycaprolactam charged was assumed. It will be understood that slightly different results may be obtained under different reactor configurations and steam flows, but we believe that the trends shown in the Figures have general validity.

FIG. 1 shows the expected rate of caprolactam production as a function of pressure at 320° C. The labels on each curve represent the pressure in the reactor in atmospheres. Thus, 1 means 1 atm, 2 means 2 atm, and so on. It is evident that increasing the pressure increases the rate of caprolactam production overhead, but the greatest impact is at relatively low pressures. For example, the rate increases the most in going from 1 atm to 2 atm, and the least in going from 5 atm to 6 atm.

Figure 2:
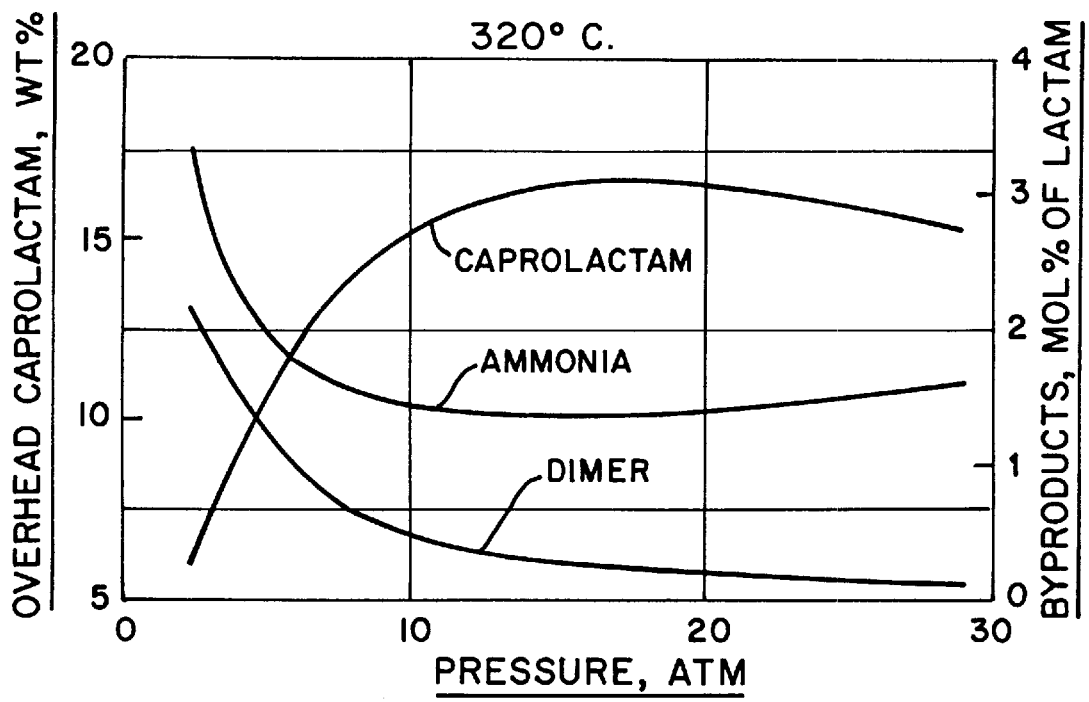
Figure 3:
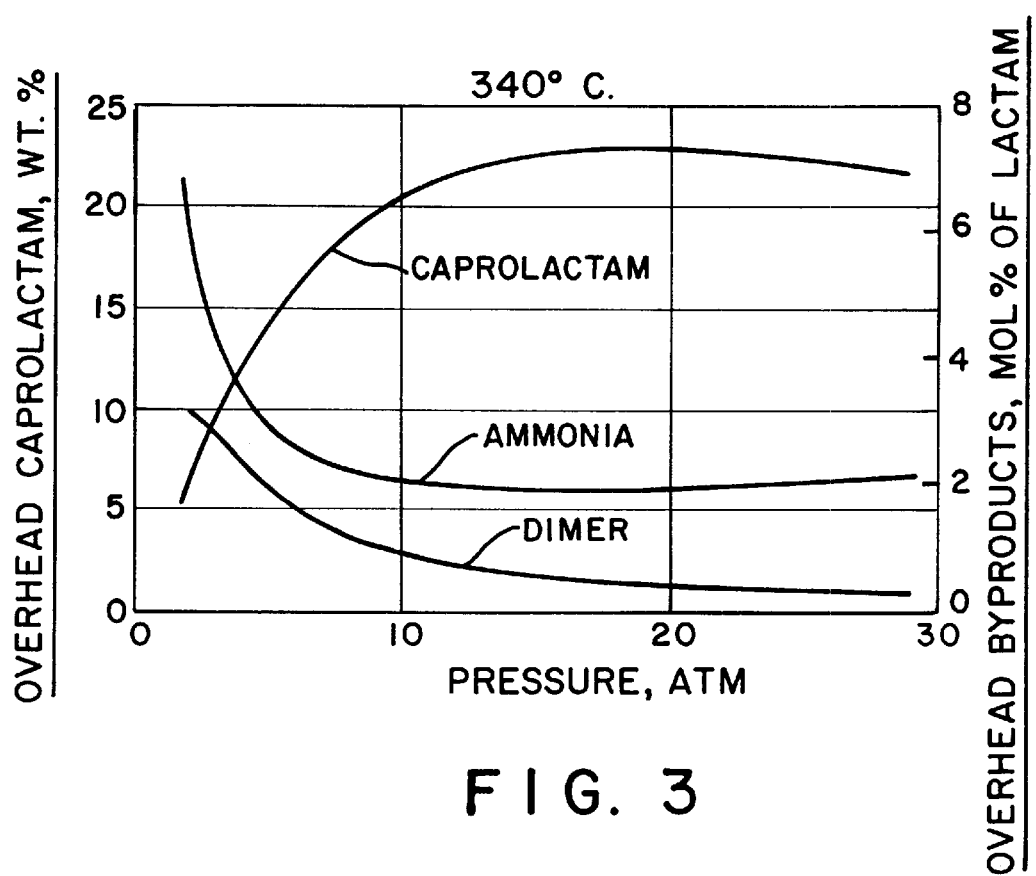

FIGS. 2 and 3 illustrate the effects of pressure and temperature on the concentration of caprolactam in the overheads at 90% caprolactam yield. Since the curves were drawn at constant steam flow, the concentration of caprolactam is proportional to the rate of caprolactam production. It is evident that at relatively low pressures the rate sharply increases with pressure but the effect diminishes at higher pressures and a maximum rate is reached at ca 17 atm at 320° C. or at 19 atm at 340° C. The Figures also show (right Y-axis) the production of cyclic dimer and ammonia relative to caprolactam. It is evident that these rates sharply decrease at lower pressures but the effect diminishes at higher pressures. In the case of ammonia, a minimum is shown at about the pressure of maximum rate of caprolactam production. The production of the cyclic dimer of caprolactam monotonically decreases with increasing pressure. Finally, comparison of the two Figures shows that increasing the temperature increases the rate of caprolactam production but even more so the rates of ammonia and dimer production.

EXAMPLE 6

For a continuous process, the apparatus comprises at least three reactors equipped with inlet at the top and outlet at the bottom for liquid flow, and inlet at the bottom and outlet at the top for vapor flow. The three reactors are connected in series so that liquid flow runs in one direction while vapor flow runs in the opposite direction. Each reactor is equipped with a mechanical agitator and baffles that ensure intimate mixing between liquid and vapor. Polycaprolactam waste is continuously fed to the first reactor by means of an extruder and exits from the last. Superheated steam is fed to the last reactor at a rate approximately 5 times the extrudate flow and exits from the first reactor. The reactors are held at about 330° C. and 15 atm. The overall residence time of the melt in the reactors is about 4 hours. The exit vapors are sent to a partial condenser where a condensate containing about 90% caprolactam is obtained. Fiber grade caprolactam may be obtained from this condensate by further purification including filtration, distillation, crystallization, and other conventional techniques known in the art. A portion of the remaining vapor is purged while the rest is mixed with makeup steam, sent to a superheater, and recycled through the process.

From the foregoing description, one skilled in the art can easily ascertain the essential characteristics of this invention, and without departing from the spirit and scope thereof, can make various changes and modifications of the invention to adapt it to various usages and conditions.

We claim:

1. A process for depolymerizing polycaprolactam waste to form caprolactam comprising the step of:

in the absence of added catalyst, contacting said polycaprolactam waste with superheated steam at a temperature of about 250° C. to about 400° C. and at a pressure within the range of 2 atm to about 100 atm and substantially less than the saturated vapor pressure of water at said temperature wherein a caprolactam-containing vapor stream is formed.

2. The process of claim 1 which further comprises the step of:

subjecting a mixture of liquid water and said polycaprolactam waste to sufficient heat and pressure for a time sufficient to reduce the molecular weight of said polycaprolactam prior to said contacting step.

3. The process of claim 1 wherein said pressure is within the range of 2 atm to about 30 atm.

4. The process of claim 1 wherein said temperature is within the range of about 280° C. to about 350° C. and said pressure is within the range of 2 atm to about 30 atm.

5. The process of claim 1 wherein said temperature is within the range of about 290° C. to about 340° C. and the pressure is within the range of about 3 atm to about 15 atm.

6. The process of claim 1 which further comprises the step of:

removing said formed caprolactam-containing vapor stream from said contact region.

7. The process of claim 6 which further comprises the step of:

separating said caprolactam from said removed caprolactam-containing vapor stream by partial condensation.

8. The process of claim 7 which further comprises the step of:

purifying said separated caprolactam.

9. A process for depolymerizing polycaprolactam waste to form caprolactam comprising the step of:

in the absence of added catalyst, contacting said polycaprolactam waste countercurrently or crosscurrently with superheated steam in a series of continuous flow stirred reactors at a temperature of about 250° C. to about 400° C. and at a pressure within the range of 2 atm to about 100 atm and substantially less than the saturated vapor pressure of water at said temperature wherein a caprolactam-containing vapor stream is formed.

10. The process of claim 9 which further comprises the step of:

subjecting a mixture of liquid water and said polycaprolactam waste to sufficient heat and pressure for a time sufficient to reduce the molecular weight of said polycaprolactam prior to said contacting step.

11. The process of claim 9 which further comprises the step of:

removing said formed caprolactam-containing vapor stream from said contact region.

12. The process of claim 11 which further comprises the step of:

separating said caprolactam from said removed caprolactam-containing vapor stream by partial condensation.

13. The process of claim 11 which further comprises the step of:

subjecting a portion of said caprolactam depleted vapor stream to superheating and recycling it to said contacting step.

14. The process of claim 12 which further comprises the step of:

purifying said separated caprolactam.

15. A process for depolymerizing polycaprolactam waste to form caprolactam comprising the step of:

in the absence of added catalyst, contacting said polycaprolactam waste countercurrently with superheated steam in a vertical tubular reactor at a temperature of about 250° C. to about 400° C. and at a pressure within the range of 2 atm to about 100 atm and substantially less than the saturated vapor pressure of water at said temperature wherein a caprolactam-containing vapor stream is formed.

16. The process of claim 15 which further comprises the step of:

subjecting a mixture of liquid water and said polycaprolactam waste to sufficient heat and pressure for a time sufficient to reduce the molecular weight of said polycaprolactam prior to said contacting step.

17. The process of claim 15 which further comprises the step of:

removing said formed caprolactam-containing vapor stream from said contact region.

18. The process of claim 17 which further comprises the step of:

separating said caprolactam from said removed caprolactam-containing vapor stream by partial condensation.

19. The process of claim 17 which further comprises the step of:

subjecting a portion of said caprolactam depleted vapor stream to superheating and recycling it to said contacting step.

20. The process of claim 18 which further comprises the step of:

purifying said separated caprolactam.

* * * * *